United States Patent
Dernoncourt

(10) Patent No.: US 9,227,854 B2
(45) Date of Patent: *Jan. 5, 2016

(54) PROCESS FOR PURIFICATION OF AN AQUEOUS PHASE CONTAINING POLYAROMATICS

(75) Inventor: Renaud Dernoncourt, Brussels (BE)

(73) Assignee: TOTAL PETROCHEMICALS FRANCE, Paris la Defense (FR)

( * ) Notice: Subject to any disclaimer, the term of this patent is extended or adjusted under 35 U.S.C. 154(b) by 1069 days.

This patent is subject to a terminal disclaimer.

(21) Appl. No.: 12/745,372

(22) PCT Filed: Nov. 21, 2008

(86) PCT No.: PCT/EP2008/066021
§ 371 (c)(1),
(2), (4) Date: Nov. 19, 2010

(87) PCT Pub. No.: WO2009/068485
PCT Pub. Date: Jun. 4, 2009

(65) Prior Publication Data
US 2011/0054135 A1    Mar. 3, 2011

(30) Foreign Application Priority Data
Nov. 29, 2007    (EP) .................................... 07291442

(51) Int. Cl.
*B01D 11/04* (2006.01)
*B01D 17/025* (2006.01)
*C02F 1/26* (2006.01)
*B01D 17/04* (2006.01)
*C07C 5/333* (2006.01)
*C02F 1/20* (2006.01)
*C02F 101/32* (2006.01)
*C02F 103/36* (2006.01)
*C02F 103/38* (2006.01)

(52) U.S. Cl.
CPC .............. *C02F 1/26* (2013.01); *B01D 11/0492* (2013.01); *B01D 17/047* (2013.01); *C07C 5/333* (2013.01); *C02F 1/20* (2013.01); *C02F 2101/327* (2013.01); *C02F 2103/36* (2013.01); *C02F 2103/38* (2013.01)

(58) Field of Classification Search
CPC ........ C02F 1/26; C02F 1/20; C02F 2101/327; C02F 2103/38; C02F 5/333; B01D 11/0492; B01D 11/04; B01D 17/047
See application file for complete search history.

(56) References Cited

U.S. PATENT DOCUMENTS

| 3,256,355 A | | 6/1966 | Gilman et al. | |
| 3,515,765 A | | 6/1970 | Berger | |
| 3,515,766 A | * | 6/1970 | Root et al. | 585/402 |
| 4,009,218 A | | 2/1977 | Uitti | |
| 4,026,791 A | * | 5/1977 | Wallace | 210/634 |
| 4,039,602 A | * | 8/1977 | Uitti | 585/441 |
| 4,235,602 A | * | 11/1980 | Meyer et al. | 210/634 |
| 4,288,234 A | | 9/1981 | Cox et al. | |
| 4,628,136 A | | 12/1986 | Sardina et al. | |
| 5,189,216 A | * | 2/1993 | Kiefer et al. | 562/600 |
| 5,595,661 A | * | 1/1997 | Li et al. | 210/634 |
| 6,388,155 B1 | * | 5/2002 | Sy et al. | 585/441 |
| 2004/0262238 A1 | | 12/2004 | Munnig | |

FOREIGN PATENT DOCUMENTS

| EP | 0767171 | | 4/1997 |
| GB | 1097619 | A | 1/1968 |
| GB | 1452729 | | 10/1976 |
| JP | 42-026774 | | 12/1967 |
| WO | 0158813 | A1 | 8/2001 |
| WO | WO 01/58813 | | 8/2001 |

OTHER PUBLICATIONS

Japanese Office Action issued in JP 2010-535342, dated Aug. 2, 2011, 4 pages.
Korean Office Action issued in KR 10-2010-7011497, dated Apr. 18, 2012, 8 pages.
Taiwanese Office Action issued in TW 097142879, dated Jun. 21, 2013, 8 pages.
Hyeungchul Choi, et al., "The Study on the thermodynamic analysis and develope alternative entrainer for the azeotropic process", Theories and Applications of Chem. Eng., 2003, vol. 9, No. 2 (pp. 2512-2515).

* cited by examiner

*Primary Examiner* — Katherine Zalasky

(57) ABSTRACT

The present invention is a process for purifying a liquid stream having an aqueous phase with polyaromatics, and optionally an organic phase. The process can include sending the liquid stream to a mixing tank and introducing an aromatic component to produce a mixture of an organic phase and of an aqueous phase. The mixture can be sent to a decanter to recover a clean aqueous phase and an organic phase. The clean aqueous phase can go through a stripper to remove a substantial part of any remaining organic component. The liquid stream can be the whole or a fraction of an aqueous phase recovered by condensation of an effluent gas leaving an ethylbenzene dehydrogenation reactor.

20 Claims, No Drawings

PROCESS FOR PURIFICATION OF AN AQUEOUS PHASE CONTAINING POLYAROMATICS

CROSS-REFERENCE TO RELATED APPLICATIONS

This application claims the benefit of PCT/EP2008/066021, filed Nov. 21, 2008, which claims priority from EP 07291442.7, filed Nov. 29, 2007.

FIELD OF THE INVENTION

The present invention relates to a process for purification of an aqueous phase containing polyaromatics. Said purification is of interest in the process of the catalytic dehydrogenation of ethylbenzene to produce styrene. Said dehydrogenation is typically carried out at temperatures within the range of about 540-660° C. under near atmospheric or even subatmospheric pressure conditions. Typically, an ethylbenzene steam feed having a steam to ethylbenzene mole ratio of 5 to 10 or even higher is passed over a dehydrogenation catalyst such as iron oxide in an adiabatic dehydrogenation reactor. Large quantities of steam are employed in order to supply a part of the sensible heat to the dehydrogenation (endothermic reaction), to reduce the partial pressure of the ethyl benzene to favor the dehydrogenation reaction, and to keep the catalyst free of coke and carbon deposits. The stream (also called the effluent gas) leaving the ethylbenzene dehydrogenation reactor contains primarily styrene, hydrogen, unreacted ethylbenzene, divinylbenzene and small amounts of benzene, toluene, methane, ethane, carbon monoxide, carbon dioxide, various polymeric materials and tars as well as an aqueous component. Said stream is treated to recover the styrene, ethylbenzene is recycled to the dehydrogenation and water can be vaporized to steam and optionally recycled with ethylbenzene. Before recycling the water as steam in the dehydrogenation or to use said water to make steam it has to be purified to remove organics as well as various polymeric materials and tars.

BACKGROUND OF THE INVENTION

The dehydrogenation has been described in various prior arts. U.S. Pat. No. 3,256,355 relates to the dehydrogenation of ethylbenzene to make styrene. In said prior art, referring to the stream leaving the ethylbenzene dehydrogenation reactor, the latent heat of condensation of the contained steam is used to heat the reboilers of distillation columns in the overall process. Said stream is firstly washed with hot water to remove tars, then compressed and sent to the reboilers.

U.S. Pat. No. 4,288,234 describes an ethylbenzene dehydrogenation wherein the stream leaving the ethylbenzene dehydrogenation reactor is introduced in a cooling zone containing one or more cooling steps and a compression step. The remaining gases, essentially hydrogen, are washed with ethylbenzene and then polyethylbenzene to remove aromatics.

U.S. Pat. No. 4,628,136 describes an ethylbenzene dehydrogenation wherein the stream leaving the ethylbenzene dehydrogenation reactor is introduced in a conventional cooling zone where are recovered (i) a gaseous phase (essentially hydrogen), (ii) an organic phase (ethylbenzene and styrene) and (iii) an aqueous phase. Said aqueous phase is further mixed with fresh ethylbenzene then is vaporized while condensing the reflux of the ethylbenzene/styrene distillation column and then sent to the dehydrogenation catalyst.

U.S. Pat. No. 6,388,155 relates to a process for the production of styrene monomer from ethylbenzene comprising the steps of:
a) catalytically dehydrogenating said ethylbenzene in the presence of steam thereby catalytically producing a dehydrogenation effluent gas containing unreacted ethylbenzene and lighter components and styrene monomer and heavier components;
b) scrubbing said effluent gas with reflux to remove at least a portion of said styrene monomer and heavier components from said effluent gas;
c) condensing said scrubbed effluent gas thereby producing a liquid organic dehydrogenation mixture, an aqueous phase and a gaseous phase; and
d) using a portion of said liquid organic dehydrogenation mixture as said reflux for said step b) of scrubbing.

In the bottoms of said scrubber of step b) an aqueous phase and an organic phase are recovered, said aqueous phase is mixed with aqueous phase recovered at step c) and said organic phase is fed to a distillation column for separation of the ethylbenzene and styrene monomer.

In said processes there are water streams containing small amounts of various polymeric materials and condensed heavy components. The polymeric materials are essentially coming from polymerization of divinylbenzene with styrene. The condensed heavy components are produced in small amounts in the dehydrogenation process. By simplification, in the following description and claims, these polymeric materials and condensed heavy components are often called polyaromatics. When said aqueous phase containing polyaromatics goes through vessels, heat exchangers, boilers etc. . . . there is a serious risk of fouling of said equipment by the polyaromatics. Moreover because these polyaromatics might be originated from divinylbenzene, a cross-linking might occur.

It has been discovered that introduction of an aromatic component, advantageously ethylbenzene or benzene or toluene or mixture thereof cause the migration of polyaromatics to an organic phase. Said organic phase is then separated from the aqueous phase in a decanter. This leads to a clean aqueous phase leaving the decanter. "Clean aqueous phase" means that said aqueous phase leaving the decanter will not induce fouling or random polymerizations in the vessels, pipes and any piece of equipment.

BRIEF DESCRIPTION OF THE INVENTION

The present invention is a process for purifying a liquid stream comprising an aqueous phase and optionally an organic phase,
said aqueous phase comprising polyaromatics in solution in water,
wherein,
a) said liquid stream is sent to a mixing tank in which is introduced an effective amount of an aromatic component, advantageously ethylbenzene or benzene or toluene or mixture thereof to produce a mixture of an organic phase and of an aqueous phase,
b) then said mixture recovered at step a) is sent to a decanter to recover a clean aqueous phase and an organic phase,
c) then the clean aqueous phase leaving the decanter of step b) goes through a stripper to remove a substantial part of any remaining organic component.

Purpose of said introduction is to cause the migration of polyaromatics to the organic phase.

When the stream sent to step a) has no organic phase, the introduction of the aromatic component at step a) creates an organic phase and said organic phase contains the aromatic component introduced at step a) and the essential part of the polyaromatics which were initially dissolved in the aqueous phase sent to a).

When the stream sent to step a) already comprises an organic phase, the introduction of the aromatic component at step a) creates a migration of the essential part of the polyaromatics to the already existing organic phase and said organic phase contains the aromatic component introduced at step a) and the essential part of the polyaromatics which were initially dissolved in the aqueous phase sent to a).

Advantageously, in step c), as much as possible of the remaining organic components are to be removed. Then said aqueous phase could be advantageously used to make steam.

According to a specific embodiment the stream sent to step a) is the whole or a fraction of the aqueous phase recovered by condensation of the effluent gas leaving an ethylbenzene dehydrogenation reactor.

DETAILED DESCRIPTION OF THE INVENTION

As regards the aqueous phase sent to step a), a part of the polyaromatics are the result of polymerization of at least a divinylaromatic monomer and optionally a monovinylaromatic monomer or any monomer able to copolymerize with the divinylaromatic monomer. As example of divinylaromatic monomer, divinylbenzene can be cited. As regards the monovinylaromatic monomer, it relates to any aromatic bearing a vinyl function. By way of example, mention may be made of styrene, vinyl toluene, alphamethylstyrene, alpha-ethylstyrene, methyl-4-styrene, methyl-3-styrene, methoxy-4-styrene, hydroxymethyl-2-styrene, ethyl-4-styrene, ethoxy-4-styrene, dimethyl-3,4-styrene, chloro-2-styrene, chloro-3-styrene, chloro-4-methyl-3-styrene, tert.-butyl-3-styrene, dichloro-2,4-styrene, dichloro-2,6-styrene, vinyl-1-naphtalene and vinylanthracene.

The polyaromatics are slightly soluble in water but it is enough to induce fouling. The amount of the polyaromatics is, by way of example, in the range 5 to 1000 ppm of the aqueous phase.

Proportions of aqueous phase and organic phase, if any, sent to step a) can be any, advantageously the aqueous phase is the major phase and preferably is 75 to 100 w % of the liquid stream.

The aromatic component introduced in the mixing tank can be any aromatic which cannot polymerize, advantageously it is ethylbenzene or benzene of toluene or mixture thereof. Amount of said aromatic component introduced is in the range of 0.05 to 5% by weight of the amount of aqueous phase. Volume of said mixing tank is designed to have a residence time in the range of 5 to 45 minutes.

Advantageously the mixing tank comprises means to mix intimately the aromatic component with the aqueous phase comprising the polyaromatics.

As regards the pressure, steps a) and b) can be operated at any pressure but it is more convenient to be at atmospheric pressure.

As regards the temperature, steps a) and b) can be operated at any temperature but it is more convenient to be at ambient temperature.

As regards the pressure of the liquid stream sent to step a) and the pressure of the aromatic component stream sent to step a) there is no requirement of one having a higher pressure than the other provided they are introduced in the mixing tank. The mixing of the liquid stream with the aromatic component stream is made essentially by the mixing equipment of the mixing tank.

As regards the stripping of step c), it is known in itself. By way of example the clean aqueous phase leaving the decanter of step b) is sent as a liquid phase (the feedstock of the stripper) on top of a column filled with trays or packing or any means to put liquid and vapor in contact. Said stripper is heated by a reboiler on the bottoms or by injection of live steam. The overhead of said stripper is a vapor phase comprising essentially steam and a major part of the organic components of the feedstock. The bottoms of said stripper is water containing essentially the remaining part of the organic components of the feedstock.

According to a specific embodiment the stream sent to step a) is the whole or a fraction of the aqueous phase recovered by condensation of the effluent gas leaving an ethylbenzene dehydrogenation reactor. The stream (also called the effluent gas) leaving an ethylbenzene dehydrogenation reactor, contains primarily styrene, hydrogen, unreacted ethylbenzene, benzene, toluene and small amounts of divinylbenzene, methane, ethane, carbon monoxide, carbon dioxide, various polymeric materials and heavy compounds as well as an aqueous component.

The effluent gas from the dehydrogenation reactor is partially cooled in a waste heat exchanger against the incoming ethylbenzene and sometimes against other streams and then fed to a main condenser. The styrene, unreacted ethylbenzene, most part of the benzene and toluene, divinylbenzene, polymeric materials, heavy compounds and the aqueous component are condensed in said main condenser while the hydrogen, methane, ethane and carbon monoxide and dioxide and the remaining part of the benzene and toluene remain in the gaseous phase. Said gaseous phase is separated and treated by means including compression followed by recovery of the benzene and toluene. From the main condenser, the now partially condensed effluent (the liquid phase leaving the main condenser) is fed to a decanter (D) (phase separator).

From said decanter (D) are recovered an aqueous phase and an organic phase which comprises primarily the crude styrene and the unreacted ethylbenzene. Said aqueous phase is sent to step a) of the above described process for purifying.

The organic phase from the decanter (D), optionally mixed with the organic phase recovered at step b), is fed to the styrene distillation train.

There are other processes to treat the effluent gas leaving an ethylbenzene dehydrogenation reactor but all the processes lead to an aqueous phase comprising polyaromatics in solution in water.

In said embodiment, wherein the stream sent to step a) is the whole or a fraction of the aqueous phase recovered by condensation of the effluent gas leaving an ethylbenzene dehydrogenation reactor, as regards the stripping of step c), advantageously the temperature of the top of the stripper is around 95° C. to 110° C. depending on the operating pressure of the stripper. Overhead of the stripper comprises water, benzene, toluene and other aromatics, is condensed and sent advantageously to a decanter, the organic phase being sent to the recovery section that separates styrene, ethylbenzene, and other impurities.

The invention claimed is:

1. A process for purifying a liquid stream comprising an aqueous phase and optionally an organic phase, said aqueous phase comprising polyaromatics in solution in water, the process comprising:
   a) sending the liquid stream to a mixing tank in which is introduced an effective amount of an aromatic component to produce a mixture of an organic phase and of an aqueous phase, wherein the effective amount is sufficient to cause migration of the polyaromatics to the organic phase, wherein the aqueous phase comprises 75 to 100 wt % of the liquid stream, and wherein the aromatic component comprises a mixture of ethylbenzene with benzene, toluene, or combinations thereof;

b) sending the mixture recovered at step a) to a decanter to recover a clean aqueous phase and an organic phase; and c) passing the clean aqueous phase leaving the decanter of step b) through a stripper to remove a substantial part of any remaining organic component, wherein the polyaromatics are condensed heavy components and the result of polymerization of at least a divinylaromatic monomer and optionally a monovinylaromatic monomer or any monomer able to copolymerize with the divinylaromatic monomer.

2. The process of claim 1, wherein the aromatic component introduced in step a) comprises a mixture of ethylbenzene with benzene.

3. The process of claim 1, wherein the stream sent to step a) is a whole or a fraction of the aqueous phase recovered by condensation of the effluent gas leaving an ethylbenzene dehydrogenation reactor.

4. The process of claim 1, wherein the effective amount is from 0.05 to 5% by weight of the aqueous phase.

5. The process of claim 1, wherein the aromatic component cannot polymerize.

6. The process of claim 1, wherein the liquid stream has a residence time in the mixing tank ranging from 5 to 45 minutes.

7. The process of claim 1, wherein the divinylaromatic monomer comprises divinylbenzene, and wherein the monovinylaromatic monomer comprises a member of the group consisting of styrene, vinyl toluene, alphamethylstyrene, alphaethylstyrene, methyl-4-styrene, methyl-3-styrene, methoxy-4-styrene, hydroxymethyl-2-styrene, ethyl-4-styrene, ethoxy-4-styrene, dimethyl-3,4-styrene, chloro-2-styrene, chloro-3-styrene, chloro-4-methyl-3-styrene, tert.-butyl-3-styrene, dichloro-2,4-styrene, dichloro-2,6-styrene, vinyl-1-naphtalene and vinyl anthracene.

8. The process of claim 1, wherein an amount of the polyaromatics in the aqueous phase ranges from 5 to 1000 ppm.

9. The process of claim 1, wherein the liquid stream comprises no organic phase prior to introduction of the aromatic component.

10. The process of claim 1, wherein the aromatic component introduced in step a) comprises a mixture of ethylbenzene and toluene.

11. The process of 1, wherein steps a) and b) are operated at ambient temperature.

12. The process of claim 1, wherein steps a) and b) are operated at atmospheric pressure.

13. The process of claim 1, wherein the temperature at a top of the stripper is from 95° C. to 110° C.

14. The process of claim 1, wherein an overhead of the stripper comprises water, benzene, and toluene, and wherein the overhead is condensed and sent to a decanter.

15. The process of claim 1, wherein the stripper is a column filled with trays or packing, wherein overhead of the stripper is a vapor phase comprising essentially steam and a major part of organic components, and wherein a bottoms of the stripper is water containing essentially a remaining part of organic components.

16. A process for purifying a liquid stream comprising:
cooling an effluent gas from an ethylbenzene dehydrogenation reactor in a waste heat exchanger;
feeding the effluent gas to a main condenser and condensing a portion of the effluent gas in the main condenser, forming a gaseous phase and a liquid phase;
feeding the liquid phase to a decanter and recovering a liquid stream and an organic phase from the decanter, wherein the liquid stream comprises an aqueous phase comprising polyaromatics in solution in water, and wherein the aqueous phase comprises 75 to 100 wt % of the liquid stream;
sending the liquid stream to a mixing tank in which is introduced an effective amount of an aromatic component to produce a mixture of an organic phase and an aqueous phase, wherein the effective amount is sufficient to cause migration of the polyaromatics to the organic phase, and wherein the aromatic component comprises a mixture of ethylbenzene with benzene, toluene, or combinations thereof;
sending the mixture from the mixing tank to a second decanter to recover a clean aqueous phase; and
passing the clean aqueous phase through a stripper to remove a substantial part of any remaining organic component, wherein the polyaromatics are condensed heavy components and the result of polymerization of at least a divinylaromatic monomer and optionally a monovinylaromatic monomer or any monomer able to copolymerize with the divinylaromatic monomer.

17. The process of claim 16, wherein the aromatic component is a mixture of ethylbenzene and benzene.

18. The process of claim 16, wherein the aromatic component is a mixture of ethylbenzene and toluene.

19. The process of claim 16, wherein the aromatic component is a mixture of ethylbenzene, benzene, and toluene.

20. The process of claim 16, wherein the aromatic component introduced in step a) comprises a mixture of ethylbenzene, benzene and toluene.

* * * * *